United States Patent
Blok et al.

(10) Patent No.: US 7,645,422 B2
(45) Date of Patent: *Jan. 12, 2010

(54) VAPOR SENSOR AND MATERIALS THEREFOR

(75) Inventors: Edward J. Blok, Wadsworth, OH (US); Praveen C. Ramamurthy, Mansfield, OH (US); Jared Starling, Mansfield, OH (US); Blase S. Amadio, Mansfield, OH (US)

(73) Assignee: Therm-O-Disc, Incorporated, Mansfield, OH (US)

( * ) Notice: Subject to any disclaimer, the term of this patent is extended or adjusted under 35 U.S.C. 154(b) by 519 days.

This patent is subject to a terminal disclaimer.

(21) Appl. No.: 11/510,942

(22) Filed: Aug. 28, 2006

(65) Prior Publication Data

US 2006/0292033 A1 Dec. 28, 2006

Related U.S. Application Data

(63) Continuation-in-part of application No. 10/411,805, filed on Apr. 11, 2003, now Pat. No. 7,138,090.

(51) Int. Cl.
G01N 33/00 (2006.01)
(52) U.S. Cl. .................. 422/57; 422/82.01; 422/50; 422/55; 422/56; 422/68.1; 422/82.02; 422/82.03; 436/149
(58) Field of Classification Search .............. 422/82.01, 422/50, 55, 56, 68.1, 82.02, 82.03, 57; 436/149
See application file for complete search history.

(56) References Cited

U.S. PATENT DOCUMENTS

| 3,045,198 A | 7/1962 | Dolan et al. |
| 3,234,180 A | 2/1966 | Wu |
| 3,848,218 A | 11/1974 | Wakabayashi et al. |
| 3,864,659 A | 2/1975 | Furuuchi et al. |
| 4,129,030 A | 12/1978 | Dolan |
| 4,224,595 A | 9/1980 | Dolan |

(Continued)

FOREIGN PATENT DOCUMENTS

EP 0 434 396 B1 11/1994

(Continued)

OTHER PUBLICATIONS

"Conductive Black: Vulcan XC72" [online], [retrieved on Aug. 28, 2006], retrieved from www.cabot-corp.com/cws/product.nsf/PDSKEY/~~~VXC72/$file/VULCAN_XC72-English.pdf?OpenElement.

(Continued)

*Primary Examiner*—Sam P Siefke
(74) *Attorney, Agent, or Firm*—Harness, Dickey & Pierce, P.L.C.

(57) ABSTRACT

The present disclosure relates to a composition for sensor films used for detecting chemical analytes within sensors, such as polymer-absorption chemiresistors (i.e., conductometric sensors). The present disclosure provides robust sensor film compositions that have low resistance, high conductivity, and greater temperature stability and sensitivity to chemical analytes, as well as methods of making these sensor films. Sensor film compositions according to the present disclosure include a matrix having a polymer resin comprising siloxane and a plurality of conductive particles including at least two distinct species.

22 Claims, 7 Drawing Sheets

U.S. PATENT DOCUMENTS

| | | | |
|---|---|---|---|
| 4,592,967 | A | 6/1986 | Komatsu et al. |
| 4,621,249 | A | 11/1986 | Uchikawa et al. |
| 4,631,952 | A | 12/1986 | Donaghey |
| 4,673,910 | A | 6/1987 | Uchikawa et al. |
| 4,686,524 | A | 8/1987 | White |
| 4,691,186 | A | 9/1987 | Shin et al. |
| 4,752,761 | A | 6/1988 | Dolan et al. |
| 5,150,603 | A | 9/1992 | Boenning et al. |
| 5,169,909 | A | 12/1992 | Okawa |
| 5,256,574 | A | 10/1993 | Neuburger et al. |
| 5,283,308 | A | 2/1994 | Bilgrien et al. |
| 5,571,401 | A | 11/1996 | Lewis et al. |
| 5,610,324 | A | 3/1997 | Lawson |
| 5,788,833 | A | 8/1998 | Lewis et al. |
| 5,891,398 | A | 4/1999 | Lewis et al. |
| 5,911,872 | A | 6/1999 | Lewis et al. |
| 5,951,846 | A | 9/1999 | Lewis et al. |
| 5,959,191 | A | 9/1999 | Lewis et al. |
| 5,979,227 | A | 11/1999 | Lawson et al. |
| 6,013,201 | A | 1/2000 | Hayashida et al. |
| 6,042,788 | A | 3/2000 | De Wit et al. |
| 6,170,318 | B1 | 1/2001 | Lewis |
| 6,342,295 | B1 | 1/2002 | Kobayashi |
| 6,433,694 | B1 | 8/2002 | Dolan et al. |
| 6,444,323 | B1 | 9/2002 | Matsumoto et al. |
| 6,455,319 | B1 | 9/2002 | Lewis et al. |
| 6,518,371 | B1 | 2/2003 | Fink et al. |
| 6,815,520 | B2 | 11/2004 | Yoneda et al. |

FOREIGN PATENT DOCUMENTS

| | | |
|---|---|---|
| EP | 0 833 421 A2 | 4/1998 |
| EP | 1 088 849 A2 | 4/2001 |
| EP | 1 215 248 | 6/2002 |
| EP | 1 254 924 | 11/2002 |
| EP | 1467199 | 10/2004 |
| EP | 1019715 | 1/2005 |
| JP | 02-309090 | 12/1990 |
| JP | 05-043823 | 2/1993 |
| JP | 07-258548 | 2/1993 |
| JP | 08-020725 | 1/1996 |
| JP | 08-120176 | 5/1996 |
| JP | 11-106657 | 4/1999 |
| JP | 2001-158856 | 6/2001 |
| JP | 2001-221225 | 8/2001 |
| RU | 1 582 597 A1 | 11/1995 |
| WO | WO 96/37547 | 11/1996 |
| WO | WO 99/53300 | 10/1999 |
| WO | WO 01/88042 A1 | 11/2001 |
| WO | WO 02/08314 | 1/2002 |
| WO | WO 02/23134 A1 | 3/2002 |
| WO | WO 02/086911 | 10/2002 |

OTHER PUBLICATIONS

"Carbon Black: Black Pearls 2000" [online], [retrieved on Aug. 28, 2006], retrieved from www.cabot-corp.com/cws/product.nsf/PDSDOCKEY/~~~BP2000?OpenDocument.

European Search Report for EP 04076097; Dated Jul. 30, 2004.

European Search Report for EP 05011207; Dated Sep. 1, 2005.

Grate, Jay, "Solubility Properties of Siloxane Polymers for Chemical Sensors", Proceedings of SPIE-The International Society for Optical Engineering, 2574 (1995), 71-7.

Ho et al., "Review of Chemical Sensors for In-Situ Monitoring of Volatile Contaminants", SAND2001-0643, Mar. 2001.

"Inco Special Products: Inco Type 210 Extra Fine Nickel Powder" [online], [retrieved on Aug. 28, 2006], retrieved from www.incosp.com/products/type_210.

Ronot et al., "Detection of chemical vapours with a specifically coated optical-fibre sensor," Sensors and Actuators B, 11 (1993) 375-381.

Ronot et al., "Optimization and performance of a specifically coated intrinsic optical-fibre sensor for the detection of alkane compounds," Sensors and Actuators A, 41-42 (1994) 529-534.

Ronot-Trioli et al., "Solubility Interactions between Organic Vapors and Specific Polymeric Claddings for Optical Fiber Sensor," Sensors and Materials, vol. 7, No. 6, (1995) 383-393.

Schierbaum, "Application of organic supramolecular and polymeric compounds for chemical sensors," Sensors and Actuators B, 18-19 (1994), 71-76.

"SGL Carbon Group: SIGRAFIL C—continuous tow carbon fiber" [online], [retrieved on Aug. 28, 2006] retrieved from www.sglcarbon.com/sgl_t/fibers/pdf/sigrafil_c_e.pdf.

"SIGRAFIL C—the carbon fiber for industrial applications" [online], [retrieved on Aug. 28, 2006], retrieved from www.sglcarbon.de/sgl_t/fibers/sigra_c.html.

"Solutions for the Rubber Industry: Carbon Black Product Information" [online], [retrieved on Aug. 28, 2006], retrieved from www.degussa-fp.com/en/publikationen/produktinformationen/gummiru.Par.0029.pFile.tmp/E_PI_Printex_XE%202.pdf.

Hansen, George "High aspect ratio sub-micron and nano-scale metal filaments" Society for the Advancement of Material and Process Engineering, vol. 41, No. 2, Mar. 2005, pp. 2-11.

Sau, K.P., Khastgir, D., Chaki, T.K., "Electrical conductivity of carbon black and carbon fibre filled silicone rubber composites" Die Angewandte Makromolekulare Chemie, vol. 288, No. 1, 1998, pp. 11-17.

VAPOR SENSOR AND MATERIALS THEREFOR

CROSS-REFERENCE TO RELATED APPLICATIONS

This application is a continuation-in-part of U.S. patent application Ser. No. 10/411,805 filed on Apr. 11, 2003, which is herein incorporated by reference in its entirety.

FIELD

The present disclosure relates to sensor films, and more particularly to sensor films that detect vapor analytes.

BACKGROUND

Detection of specific target analytes, or chemical compounds, is important for many applications, including for example, detecting whether the concentration of analytes exceeds flammability limits. Target analytes are detected by sensors operating according to different detection mechanisms, known in the art. Most sensors employ a sensing component that is physically modified in the presence of specific analytes present in the environment. Thus, a sensor typically comprises a probe that includes both the sensing component and a probe body housing (including terminals for transmitting an output). The terminals are typically coupled to a processor, also part of the sensor, which analyzes the outputs received from the sensor probe to a user interface. Such a user interface typically contains an indicating device which signals a user when concentration values of an analyte have been exceeded.

Many sensors employ a sensing component that is a sensor film. Many sensor films swell, increasing in volume, while in the presence of the analytes. Various sensors available in the art utilize the physical changes in the sensor film to determine concentration of analyte present. Such sensors may include optical sensors, such as fiber optic sensors, where a beam of light is projected through an optical fiber at a sensor film cladding, and physical changes (e.g., refractive index or color) in the film are monitored. Such changes in refractive index occur when analytes are absorbed and change the physical properties of the cladding (including volumetric changes). Other sensors include surface acoustic wave sensors (SAWS), which project ultrasonic waves through the sensor film between transducers, and likewise detect any modifications in the properties of the sensor film (primarily the mass), translating those changes to the concentration of analyte present.

Another type of sensor film is a conductometric sensor, more particularly, a polymer-absorption chemiresistor sensor. A polymer-absorption chemiresistor has a polymer film sensor exposed to a surrounding atmosphere containing target analytes (chemical compounds). An electrical charge is applied across the polymer film. The polymer absorbs target analytes and this results in a volumetric change of the film, and hence the electrical resistance of the film.

Further, conductive particles may be distributed throughout the polymer film to enhance the sensitivity to resistance changes in the material when the volume of the polymer changes. However, any sensor film that relies upon physical changes resulting from absorption of the chemical analytes (i.e., volume, mass, refractive index, and resistance) is generally also sensitive to volumetric changes dependent on temperature. Further, enhancing the sensitivity to chemical analytes is desirable. Additionally, there are many applications where only a low amount of current is available and require low resistance sensors. There is a need for a low resistance sensor film composition that enhances sensitivity to desired chemical analytes, while further increasing its stability during temperature fluctuations.

SUMMARY

In one aspect, the present disclosure provides a conductometric sensor film for detecting one or more chemical analytes comprising a polymer matrix comprising a crosslinked polymer resin and a plurality of conductive particles. The crosslinked polymer comprises a siloxane monomer. The plurality of conductive particles preferably comprises at least two distinct species of conductive particles. A first species of the conductive particles comprises a low surface area, large diameter carbon black having an $N_2$ adsorption of between about 8 to about 25 $m^2/g$ and a DBP of about 1 to about 180 ml/100 g. In the presence of one or more chemical analytes the sensor matrix exhibits a change in resistance.

In another aspect, the present disclosure provides a low resistance conductometric sensor film for detecting chemical analytes. The sensor film comprises a polymer matrix comprising a polymer resin and a plurality of conductive particles homogeneously distributed within the polymer. The polymer comprises a siloxane monomer having at least one hydrocarbon side group with greater than or equal to two carbon atoms. The plurality of conductive particles comprises at least two distinct species of conductive particles. A first species of the conductive particles comprises carbon black. The base resistance of the sensor matrix exhibits a resistance that is less than about 700 Ohms.

In another aspect, the present disclosure provides a low resistance conductometric sensor film for detecting chemical analytes comprising: a polymer matrix comprising a polymer resin and a plurality of conductive particles. The particles are homogeneously distributed within the polymer. The polymer comprises a siloxane monomer having at least one hydrocarbon side group with greater than or equal to two carbon atoms. Further, the plurality of conductive particles preferably comprises at least two distinct species of conductive particles. The first species of the conductive particles preferably comprises a low surface area, large diameter carbon black having an $N_2$ adsorption of between about 8 to about 25 $m^2/g$, a DBP of about 1 to about 180 ml/100 g. A second species is selected from the group consisting of: high conductivity carbon black, a conductive axial geometry particle comprising carbon, and particles comprising nickel. When the sensor is in the presence of one or more chemical analytes the sensor matrix exhibits a change in resistance.

Further areas of applicability of the present disclosure will become apparent from the description provided hereinafter. It should be understood that the detailed description and specific examples, while indicating various embodiments of the disclosure, are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

The following description is merely exemplary in nature and is in no way intended to limit the disclosure, its application, or uses.

The present disclosure contemplates a sensor film having improved temperature stability and sensitivity to analytes. Thus, the sensor films exhibit a change in resistance when exposed to one or more analytes. Further, in various embodiments of the present disclosure, the sensor film in the sensor exhibits a relatively low base resistance. There are various challenges associated with the development of robust sensor films that have superior sensitivity to one or more chemical analytes, while exhibiting stability to temperature fluctuations, particularly for low resistance applications. In particular, there are challenges associated with the selection of conductive particles for use in the polymer matrix forming the sensor film. Often, it is difficult to stabilize and maintain a homogeneous distribution of such conductive particles due to potential phase separation and migration within the matrix. Preferably sensors are robust and capable of withstanding mechanical shock, vibration, and thermal shock, which includes maintaining a substantially homogeneous distribution of the plurality of conductive particles for long durations through use. Further, certain otherwise desirable conductive particle species may be difficult to process. Thus, in accordance with various embodiments of the present disclosure, a conductive polymer matrix comprises a polymer resin and a plurality of conductive particles comprising at least two distinct species, where the conductive particles are substantially homogeneously distributed within the matrix. The combination of conductive particle species demonstrates compatibility with one another and the polymer resin, improved stability, improved analyte detection, improved conductivity and hence low resistance.

Figure 1:
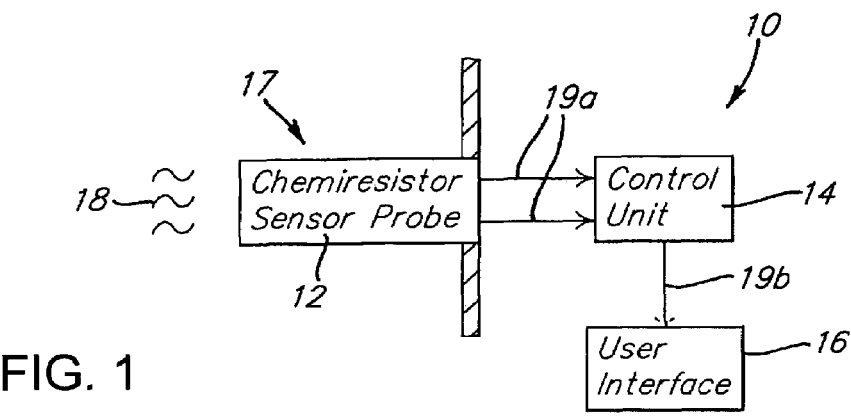
FIG. 1 is a schematic illustration of operational principles of an exemplary chemiresistor sensor.

By way of background, FIG. 1 generally depicts the major components and operational principles of an exemplary chemiresistor sensor at 10. The sensor 10 is generally comprised of a chemiresistor sensor probe 12, a control unit 14, and a user interface 16. The sensor probe 12 interacts with an external environment 17 to detect the presence of analytes, or target chemical compositions 18. The sensor probe 12 generates a raw output signal 19a based on continuous detection of analytes 18 in the external environment 17. The raw output signal 19a is processed by the control unit 14. The control unit 14 transmits a calculated output signal 19b to the user interface 16 to relay analysis of the raw output signal 19a from the sensor probe 12. The user interface 16 provides information to an external user about the sensor 10 and may range from a simple alarm signal to a complex computerized screen.

Figure 2:
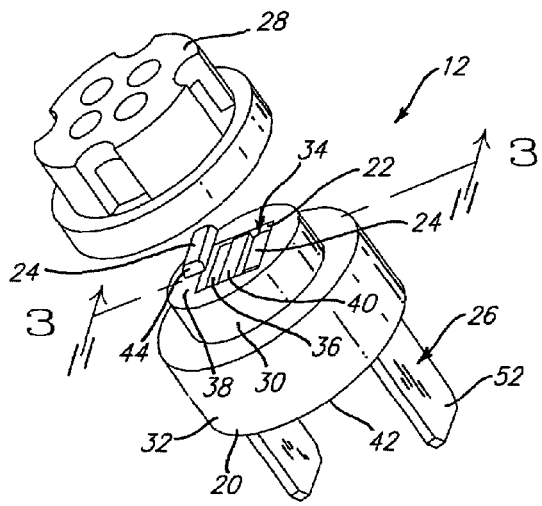
FIG. 2 is a schematic illustration of an exemplary chemiresistor sensor that can be used in accordance with the present disclosure.

Referring generally to FIG. 2, an example of a polymer-absorption chemiresistor sensor probe 12 compatible with the sensor film compositions of the teachings of the present disclosure is shown. The sensor probe 12 generally comprises a sensor housing 20, a conductive sensor film 22 covering a portion of the sensor housing 20 (FIGS. 2 and 3), a pair of electrodes 24 optionally disposed beneath and attached to the sensor terminals 26, and a protective cap 28. In lieu of electrodes, an alternate sensor embodiment is feasible, where the terminals 26 protrude into the sensor film 22, and serve a similar function to the electrodes 24 (i.e., deliver current through the sensor film 22).

The sensor housing 20 includes a first diameter portion 30 and a second diameter portion 32, wherein the first diameter portion is smaller in diameter than the second diameter portion. The first diameter portion 30 includes a sensing region 34. The sensing region 34 is comprised of two apertures 36 located within a first control surface 38 of the sensing region 34. Between the apertures 36 is a recessed second control surface 40 that extends across the sensing region 34. The second control surface 40 is slightly recessed below the first control surface 38.

Figure 3:
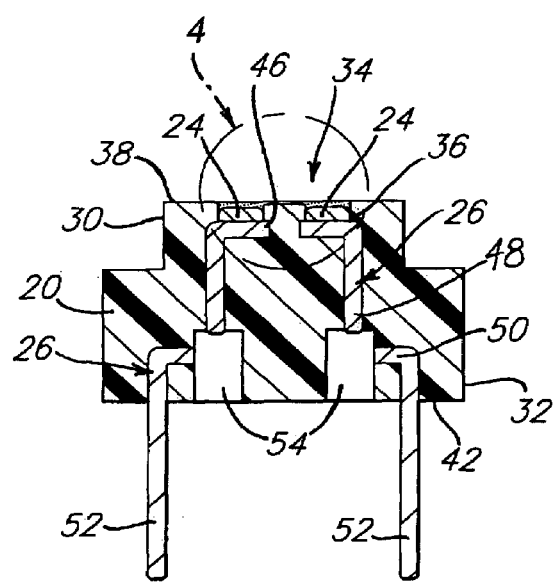
FIG. 3 is a cross-sectional view taken along line 3-3 of FIG. 2.
Figure 4:
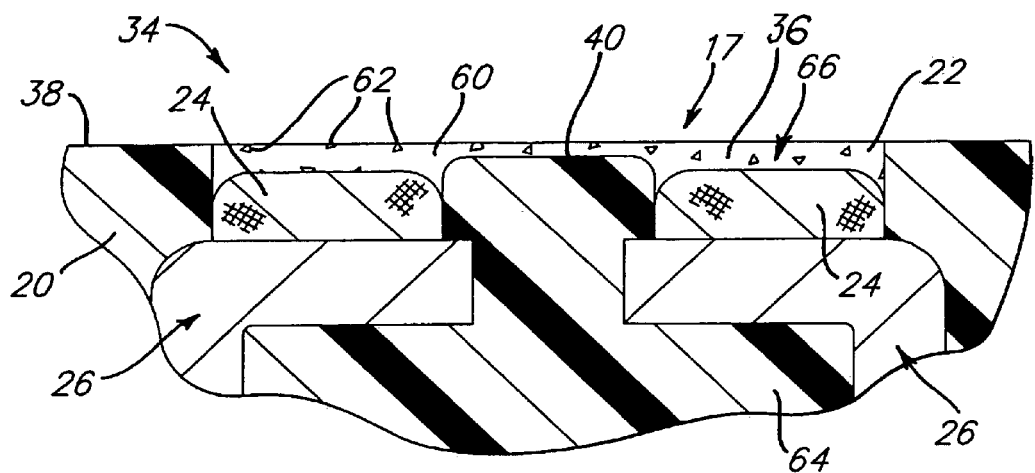
FIG. 4 is a detailed view of an exemplary sensor film region.

As best shown in FIG. 3, a cross-sectional view along line 3-3 of FIG. 2, each electrode 24 sits above the apertures 36. Terminals 26 are attached to the electrodes 24 and extend through both the first diameter portion 30 and the second diameter portion 32. The terminals 26 protrude from the housing 20 at an underside 42 of the second diameter portion 32. The electrodes 24 and terminals 26 are made of a conductive material, preferably a metal. With specific reference to FIG. 4, the electrodes 24 each comprise a horizontal porous plate or mesh that is parallel to the first control surface 38 and approximately equals the width of the aperture 36. Each electrode 24 is connected to establish a conductive pathway to terminal 26. With renewed reference to FIGS. 2 and 3, a first horizontal portion 46 of the terminal 26 makes either direct or indirect contact with the portion of the sensor film 22 seated within the apertures 36 to detect changes in the resistance of the sensor film 22. Extending from the first horizontal portion 46 is a first vertical portion 48. The first vertical portion 48 extends through the first diameter portion 30 and into the second diameter portion 32 where the first vertical portion 48 transitions to an inner terminal dogleg 50 that ends in the external terminals 52 (i.e., end leads).

At the transition point between the first vertical portion 48 to the inner terminal dogleg 50, the terminals 26 each have an aperture 54. The aperture 54 receives an alignment rod (not shown) during manufacturing to permit more precise alignment of the electrodes 24 within the housing 20. The inner terminal dogleg 50 extends to the external terminals 52 which extend from the underside 42 of the second diameter portion 32. The external terminals 52 extend from the housing 20 to a suitable length to permit interconnecting the leads to a corresponding outlet (not shown) of a suitable alert device, such as an alarm.

As best seen in FIG. 3, a detailed view of the sensing region 34 from FIGS. 1 and 2, the sensor film 22 comprises a polymer 60 with conductive particles 62 dispersed throughout. The terminals 26 extend through a body 64 of the sensor probe housing 20 and are electrically connected to the electrodes 24. The electrodes 24 protrude into the sensing region 34 and into the sensor film 22. The electrodes 24 preferably are situated near the surface, and further across the sensor film, for even current distribution. A preferable configuration of the sensor film 22 includes conductive particles 62 distributed homogeneously (i.e., evenly) throughout the sensor film 22 body forming a conductive polymeric matrix 66. By "homogeneous" it is meant that the particles are substantially evenly distributed throughout the matrix, such that any potential detrimental effects resulting from uneven and/or localized charge distribution are minimized. "Matrix" refers generally to a polymer system having conductive filler particles distributed throughout within a polymer resin.

The conductive sensor film matrix 66 is seated upon the first control surface 38 such that the matrix 66 fills the apertures 36 and spans the center second control surface 40. The matrix 66 fills the apertures 36 so that the matrix 66 is in either direct or indirect electrical contact with both of the electrodes 24. Upon exposure of the matrix 66 to target analytes, the matrix 66 volume increases by swelling.

The polymer resin 60 of the sensor film 22 can be any polymer that readily absorbs a target analyte or chemical compound, through a gas-solid interface occurring between a surface of the sensor film 22 and the surrounding gas in the external environment 17 (FIG. 1) at a rate that is relatively proportional to the concentration of the analyte in the surrounding gas. Thus, a correlation can be made between the quantity of analyte absorbed, and the concentration of the analyte in the surrounding gas. In the exemplary sensor probe 12 depicted, the change in the volume of the sensor film 22 is correlated to the concentration of the analyte present in the gas and is further related to the resistance of the sensor film 22. Of particular interest are sensor films 22 that detect vaporous hydrocarbon compound analytes, such as one or more volatile organic compounds (VOCs). Compatible polymers for detecting VOCs include siloxane polymers. A variety of siloxane based polymers are contemplated in the present disclosure, and further discussed below.

Figure 5:
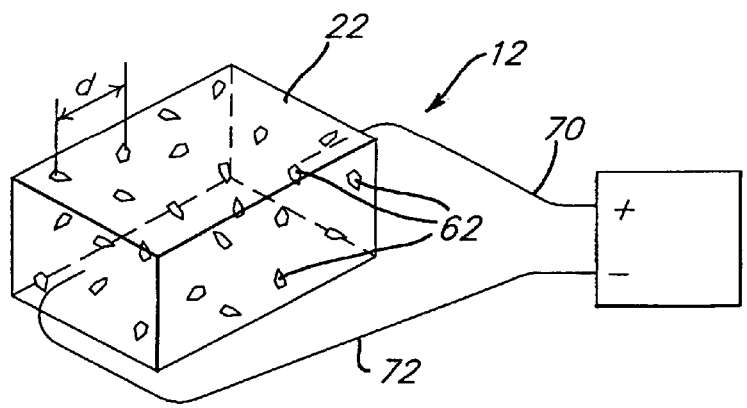
FIG. 5 is a schematic illustration of operating principles of a matrix polymer film of a polymer absorption chemiresistor.

As shown in FIG. 5, the operational principle of a polymer-absorption chemiresistor sensor probe 12 involves applying a current through the sensor film 22 between a positive 70 and a negative lead 72. Preferably, the positive and negative leads 70, 72 are electrodes, such as those shown at 24 in FIGS. 2 and 3. Conductive particles 62 are distributed throughout the sensor film 22 to enhance the electrical conductivity. Resistance measurements are taken across the sensor film 22 via monitoring of the current and potential difference across the sensor film 22 between the negative and positive leads 70, 72, and typically is measured by the processing or control unit 14 (FIG. 1) attached to the sensor probe 12. Resistance values vary with the distance "d" between the conductive particles. As this distance "d" between the conductive particles 62 increases, the resistance has a proportional relationship and thus increases. If the distance "d" decreases, the resistance also decreases. Thus, any increase or decrease in the volume of the sensor film 22 affects the overall resistance measurements. Upon detection of a change in resistance between the positive and negative leads 70,72, the user interface 16 (FIG. 1) provides a signal indicating the presence of the substance for which the sensor film 22 has an affinity. Consequently, the change in resistance of the sensor film 22 detected by the electrodes 70, 72 indicates the presence of the target analyte. The sensor film 22 volume may increase both by changes in temperature, as well as absorption of chemical compounds, or target analytes, into the polymer of the sensor film 22. One aspect of the present disclosure relates to minimizing effects of volume changes of the sensor film 22 due to temperature, and maximizing the absorption and sensor film 22 sensitivity to chemical compounds. Further, as appreciated by one of skill in the art, it is desirable to have a substantially homogenous distribution of the plurality of conductive particles 62 within the sensor film 22 to negate any potential localized variations that might occur.

Further, the long-term stability and maintenance of particle distribution is important to the accuracy of the device for long-term use. Potential phase separation and migration of the particles through the matrix can cause spatial variations of the conductive particles across the sensor film that can impact the capability of the sensor film to accurately measure the presence of the target analyte compounds. Long-term accuracy is a crucial parameter for sensor operation. Further, in some embodiments of the present disclosure, the sensor is suitable for use in a low-current application. An enhanced conductivity of the plurality of conductive particles can contribute to a reduction in the amount of current that must be applied, and hence improved conductivity permits the certain embodiments of the present disclosure to be used as low resistance sensors in low current/low resistance applications. By "low resistance" it is meant that a base resistance exhibited by the sensor film matrix is less than or equal to about 1 kOhm, more preferably less than or equal to about 700 Ohms, optionally less than or equal to about 100 Ohms, optionally less than or equal to about 50 Ohms, optionally less than or equal to about 1 Ohm, and in some aspects less than or equal to about 100 mOhms, and in some embodiments, less than or equal to about 50 mOhms. The base resistance can be obtained by measuring the resistance at time 0 and at a room temperature and pressure (e.g., 21-26° C. and 1 atm psia) before exposure to analytes. For very low current applications, such as those which operate remotely with a mobile power source, for example, a battery, it is preferable that the base resistance of the sensor is less than or equal to about 50 Ohms, optionally less than or equal to about 10 Ohms, optionally less than or equal to about 1 Ohm, optionally less than about 500 mOhms, optionally less than about 100 mOhms, and in some cases, less than or equal to about 50 mOhms.

"About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates a possible variation of up to 5% in the value.

Further, it is preferable that sensor films have efficient and improved sensitivity to one or more target chemical analytes, while minimizing cross-sensitivity to temperature (many chemiresistor films exhibit increased resistance upon exposure to an increase in temperature, independent of the concentration of the analyte). Such functions of the sensor can be expressed by overall resistance, as well as a "Vapor Ratio" and a "Temperature Ratio". The Vapor Ratio is calculated by taking the measurement of the resistance of the sensor film upon exposure to a target analyte at 0 seconds and 20 seconds, and dividing the 20 second resistance value by the 0 second value. Preferably, the vapor ratio is maximized as much as possible. Thus, it is preferred that the vapor ratio is greater than about 10, more preferably greater than about 20, and even more preferably greater than about 25. For establishing the temperature ratio, the resistance is measured at a first temperature of 25° C. and a second temperature of 65° C., where the temperature ratio is the resistance value at 65° C. divided by the resistance value at 25° C. Ideally, the temperature ratio approaches zero to reflect no variations in resistance which are attributed to changes in temperature. Practically, it is preferred that the temperature ratio is less than about 5, more preferably less than about 3.

Thus, in various embodiments, the present disclosure provides a polymer matrix having a plurality of conductive particles that comprise a combination of at least two distinct species of conductive particles to enhance sensor operations. Most preferably, the first species of conductive particles will comprise carbon black, however any number of combinations of conductive particles are contemplated by the present disclosure.

In accordance with various embodiments of the present disclosure, one species of the present disclosure preferably comprises a particularly efficacious carbon black material that has relatively low surface area values and DBP absorption values, in essence, conductive particles that are larger in particle size and lower in aggregate size. Carbon black particles may be characterized by particle size, surface area per weight, and structure. A correlation generally exists between surface area and particle size, where a smaller particle diameter gives rise to a higher surface area. Likewise, a lower surface area value generally indicates a larger particle size diameter. Surface area is generally tested by the level of nitrogen adsorption ($N_2$) values in $m^2/g$. Testing procedures for nitrogen adsorption are outlined for example, in ASTM test D3037-91. Conductive carbon black particles for use as one species in accordance with the present disclosure preferably have a $N_2$ adsorption value (surface area per weight) of between about 8 to about 25 $m^2/g$. The most preferred ranges of $N_2$ adsorption for these carbon black species are between about 10 to about 15 $m^2/g$.

Conductive carbon black particles are characterized by structure, or the configuration, of individual particles forming an aggregate. Structure can be tested by oil dibutylphthalate (DBP) absorption in accordance with test procedure ASTM D2414, where DBP is added to 100 grams of carbon black while being mixed to generate a value of DBP ml/100 grams. A sharp increase in the torque determines the DBP value. This test indicates the structure of the particles by measuring the size of the particle aggregate. When one of the species of the plurality of conductive particles is selected to be carbon black, the DBP preferably ranges from about 1 to about 180 ml/100 g.

Carbon blacks can be formed by a variety of processing conditions, and the method of formation often relates to the physical parameters of the carbon black. Two main forms of carbon black are thermal black, formed by thermal decomposition, or cracking, of natural gas. Furnace blacks are formed in an incomplete combustion furnace process, which typically entails burning or oxidizing of a carbon rich oil-based feedstock at high temperatures. Furnace blacks generally have a small particle size, as where thermal blacks tend to have the largest particle sizes of carbon blacks. Fine thermal blacks typically have an average particle size in the range of about 100 to 200 nm, and fall into the class of carbon blacks designated N800 series. One particularly preferred fine thermal black is the class N880, which varies in average particle size, but is generally between about 90 to 120 nm. Examples of commercially available conductive carbon black particles that fulfill the preferred physical characteristic ranges for one of species of conductive particles as described above include: Asahi 15HS or AS N880, both manufactured by Asahi Carbon Co., Ltd. of Japan; or CC N880 from Cancarb Ltd. of Alberta, Canada; and Spheron® 5000 or Spheron® 6000 both available from the Cabot Corporation of Boston, Mass. Preferred ranges of the mean particle size are from about 90 to about 400 nanometers, preferably less than 200 nm, and most preferably less than about 150 nm. One particularly preferred large particle size carbon black is the Asahi 15HS, which has an average particle size of between about 100 to about 130 nm, an $N_2$ adsorption of about 14 $m^2/g$, a DBP of about 85 ml/100 g, and a density of about 1.8 g/cc.

Figure 6:
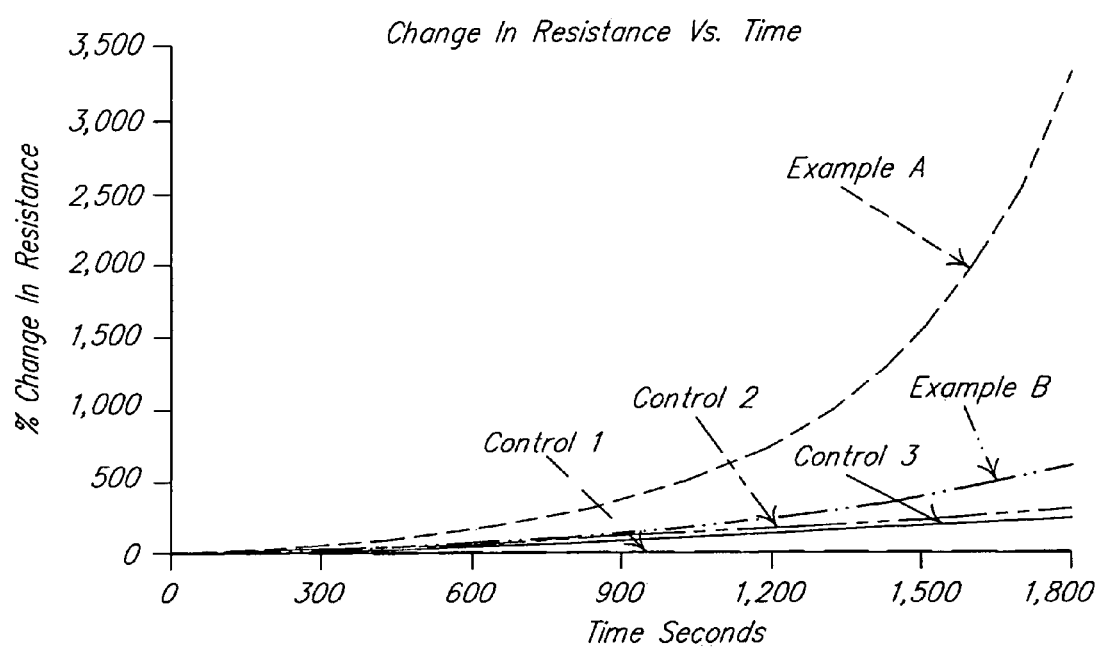
FIG. 6 is a chart of resistance versus time comparing prior art conductive particle sensor matrices with one aspect of the present disclosure.

It has been demonstrated that use of the preferred conductive carbon black particles as described above as one species of conductive particles in chemiresistor sensor films 22, significantly enhances the sensitivity of the sensor film 22 to chemical analytes over the prior art use of conductive particles. In FIG. 6, experimental data charting the percentage change of resistance versus time displays sensor sensitivity to exposure to 50 ml of 2-methylbutane solvent in a 8.5 liter container where the probes are positioned 14.3 cm above the solvent. All of the controls and examples described herein are prepared with 3-5% vinylmethylsiloxane-35-75% octylmethylsiloxane-20-62% dimethylsiloxane terpolymer (available as VAT 4326 from Gelest). Control 1 is a typical conductive carbon black particle used in chemiresistor sensors having an $N_2$ value of 1475 $m^2/g$ and a DBP value of 365 ml/100 g, and is commercially available as EC 300J from Azko Nobel Company, Chicago, Ill. Control 2 has also been previously used as a chemiresistor sensor conductive carbon black and has an $N_2$ value of 26 $m^2/g$ and a DBP value of 65 ml/100 g and is commercially available as the product Raven® 410 P from Columbian Chemicals of Marietta, Ga. Control 3 is a matrix with conventional conductive carbon black having an $N_2$ value of 43 $m^2/g$ and a DBP of 121 ml/100 g N550 available commercially from Cabot Corporation. Example A is a low surface area, large diameter conductive particle in a sensor film having an $N_2$ value of 14 and a DBP value of 85 ml/100 g. The conductive carbon black particles in Example A are commercially available, for example, from Asahi Carbon Company, Ltd. in Niigata, Japan under the trade name Asahi 15HS. Example B also has large conductive particles with low surface area having an $N_2$ value of 10 $m^2/g$ and a DBP of 30 ml/100 g which are commercially available as N880 from Cancarb, Ltd. located in Alberta, Canada. As shown in FIG. 6, the carbon black in Examples A and B demonstrate increased resistance for shorter time durations when compared with Controls 1, 2, and 3. The more rapid change in resistance of Examples A and B indicates increased sensitivity to the presence of analytes in the surrounding environment. Further, Table 1 below also includes data showing the time to reach resistance at 65° C. and the value of 2 times resistance at 65° C., and time taken to reach the corresponding value, demonstrating improved response time for Examples A and B.

TABLE 1

|  | Control 1 | Control 2 | Control 3 | Example A | Example B |
|---|---|---|---|---|---|
| 3-5% vinylmethylsiloxane - 35-75% octylmethylsiloxane - | 96.9 | 96.9 | 96.9 | 96.9 | 96.9 |

TABLE 1-continued

|  | Control 1 | Control 2 | Control 3 | Example A | Example B |
|---|---|---|---|---|---|
| 20-62% dimethylsiloxane terpolymer (%) |  |  |  |  |  |
| Carbon Black (phr) | 5 | 55 | 35 | 175 | 50 |
| Resistance at 25° C. (kOhm) | 18.0 | 23.9 | 20.3 | 26.9 | 28.0 |
| Resistance at 65° C. (kOhm) | 17.8 | 31.9 | 28.1 | 48.0 | 73.7 |
| 2X Resistance at 65° C. (kOhm) | 35.5 | 63.7 | 56.2 | 95.9 | 147.3 |
| Time to reach 2X resistance at 65° C. (seconds) | >1800 | 1320 | 1335 | 1215 | 975 |

In accordance with various embodiments of the present disclosure, the plurality of conductive particles preferably comprises a blend of conductive particles, which includes at least two species, thus, a first and a second species of conductive particles. It is preferred that the second species is a conductive particle that is compatible with the first species and the polymer resin. Where the first species is selected to be a large particle diameter low surface area carbon black, it has been observed that such particles generally have an average to low electrical conductivity. Electrical conductivity of particles is generally expressed as resistance. In certain embodiments, the second species has a higher electrical conductivity or lower resistance than the first species. Further, as described in more detail below, in certain embodiments, it is preferred that the first species is present at higher concentrations in the matrix than the second species, so that the combination of the distinct species provides unexpectedly improved performance of the sensor, even while the higher conductivity second species is present at relatively low concentrations. In various embodiments, the combination of distinct species of conductive particles including a first species that has improved sensitivity to chemical analytes and stability with temperature fluctuations combined with a second species that has a high electrical conductivity, but provide at relatively low concentrations, provides an improved conductivity and reduced resistance of the sensor film matrix.

In certain embodiments, one species is selected to be an electrically conductive metal particle. As appreciated by one of skill in the art, metal particles tend to have high densities and relatively high average particle sizes, thus typical conductive metal particles exhibit separation in polymer matrix films. Selection of the conductive metal particles is highly dependent on physical similarity to the other species of conductive particle selected in the plurality. In certain embodiments, the low surface area, large diameter carbon black particles comprise the first species, and in such embodiments, it is preferred that the conductive metal particle has similar physical properties to the other species.

Examples of such electrically conductive metals include nickel, gold, silver, manganese, copper, iron, cobalt, magnesium, aluminum, mixtures and alloys thereof. Particularly preferred electrically conductive metal particles include gold and silver. One particularly preferred conductive metal is nickel. Conductive nickel components have relatively high electrical conductivity, good chemical and physical stability, and similar physical size (about 5 times the particle diameter of the preferred carbon black compounds) and a relatively low density to the embodiment where a large particle size carbon black is the first species. Thus, in certain embodiments, the preferred average particle size for the nickel particles is about 200 to about 500 nm. Further, nickel has a density of about 9 g/cc. In other embodiments, the conductive particles comprise gold and/or silver, which each respectively having a density of around 10 g/cc, and have a maximum particle size of about 500 nm. It has been observed that where a large particle size carbon black is selected as the first species and particles comprising nickel are selected as the second species, the conductive particles are stable in the matrix and do not suffer from phase separation after longer durations. In certain embodiments, where the first conductive particle species is a large particle size carbon black and the second conductive particle species comprises nickel, the sensor film exhibits a base resistance of less than or equal to about 700 Ohms, optionally less than or equal to about 600 Ohms.

One example of a suitable conductive nickel particle is a filamentary nickel powder with a fine structure and high surface area, having an average particle size of about 500 nm to about 1 µm, an apparent density of about 0.5 g/cc, and a BET surface area of about 1.5 to about 2.5 $m^2/g$, commercially available as Extra Fine Nickel Powder Type 210 from Inco Ltd., of Wyckoff, N.J., and has an average particle size of about 200 to about 500 nm. Where the conductometric sensor film comprises a plurality of particles where a first species is a low surface area large particle carbon black and a second species is a conductive nickel powder, it is preferred that the first species is provided at about 140 parts per hundred resin (phr) and the second species is present at about 30 to about 40 parts per hundred resin (phr). In certain embodiments, a ratio of the low surface area large particle diameter first species to a nickel powder second species is from about 3:1 to about 10:1 on a weight basis.

In certain embodiments, one species comprises a high conductivity carbon black particle. As described above, a large particle size carbon black has a resistance of greater than about 1 kOhm, meaning it has a relatively low conductivity. In certain embodiments, such a low conductivity carbon black particle can be combined with a high conductivity particle. In some embodiments, such a high conductivity particle is a high conductivity carbon black. In certain aspects, "high conductivity" generally refers to carbon black particles having a resistance of less than about 100 Ohm, optionally less than about 10 Ohm, which include super-conductive, extra-conductive carbon blacks. Such high conductivity carbon black particles have a typical $N_2$ adsorption value (surface area per weight) of from about 35 to about 1500 $m^2/g$, and densities of about 1.6 to about 1.8 g/cc. Generally, it is believed that highly conductive carbon black particles have high surface areas. Further, such particles preferably have an average particle size of less than about 130 μm, optionally less than about 100 μm, optionally less than 50 μm and optionally less than about 1 μm, optionally less than about 400 nm, in some embodiments less than about 150 nm, and in certain embodiments from about 12 to 40 nm. The DBP absorption reflects high structure, preferably greater than about 150 ml/100 g, and in certain embodiments greater than 300 ml/100 g. In certain embodiments, where the first conductive particle species is a large particle size low conductivity carbon black and the second species is a high conductivity carbon black, the sensor film exhibits a base resistance of less than or equal to about 50 Ohms.

It should be noted that high conductivity carbon black particles generally have a high structure, which makes them readily absorb polymer resin during processing. As such, when these high structure particles are mixed into the polymer resin to form the matrix, the viscosity is significantly increased, which increases the difficulty of using such materials during processing. In accordance with certain embodiments of the present disclosure, the high conductivity carbon black particles are included in the plurality of conductive particles at a concentration that does not adversely affect the processing and assembly of the sensor film materials, but promotes conductivity and enables the formation of a low resistance sensor. Further, as demonstrated in FIG. 6, where a high conductivity carbon black (i.e., EC 300 J in Control 1) is used by itself in a sensor matrix, it is not as effective at sensing target analytes as the low surface area, large particle diameter carbon blacks of Examples A and B.

Examples of suitable high conductivity carbon black particles include, by way of example, VULCAN® XC-72, BLACK PEARLS® 2000, both commercially available from Cabot Corp., KETJEN® EC-300J and KETJEN® EC-600J, both available from Azko Nobel, and Printex® XE-2 available from Degussa of Germany. Particularly preferred high conductivity carbon blacks include the BLACK PEARLS® 2000, KETJEN® EC-300J and EC 600J In embodiments where the first species comprises a large particle diameter, low surface area carbon black and the second species comprises a high conductivity, high surface area carbon black, a ratio of the first species to the second species, on a weight basis is from about 8:1 to about 15:1. In certain embodiments, the first conductive species is present at about 140 to about 150 parts per hundred resin, and the second conductive species is present at about 10 to about 15 parts per hundred resin. Variations in the concentrations and ratios of the first species and second species are contemplated by the present disclosure, as the concentration of the highly conductive second species increases, the sensor film resistance decreases, however, there is a trade-off with difficulty in processing and further potential loss of sensitivity to target analytes (for example, as the large particle size, low surface area carbon black concentration decreases).

In certain embodiments, the sensor film matrix having conductive particles comprises a species comprising a conductive particle having an axial geometry, such as fibers, wires, whiskers, filaments, and the like. Such particles having a cylindrical or rod shape with an elongated axis have an axial geometry. Generally, an aspect ratio (AR) for cylindrical shapes (e.g., a rod or fiber) is defined as AR=L/D where L is the length of the longest axis and D is the diameter of the cylinder or fiber. Exemplary axial geometry particles suitable for use in the present disclosure generally have high aspect ratios, ranging from about 500 to 5,000, for example.

One particular type of conductive axial geometry particle is a fiber. A suitable fiber comprises carbon, and can be in the form of graphite (i.e., hexagonally crystallized carbon). A carbon fiber is generally produced by carbonizing or graphitizing precursor fibers based on polyacrylonitrile (PAN), petroleum pitch, or rayon. Carbon fibers and graphite fibers are made and heat-treated at different temperatures; however each has different carbon content. Carbon fibers are often designated by "tow" which is an untwisted bundle of continuous filaments, and usually designated by a number in thousands (designated by k after the respective tow number). One suitable carbon fiber is a milled or pelletized carbon fiber that is derived from PAN precursor that has high electrical conductivity, high strength, high modulus of elasticity, and low density. One such carbon fiber is commercially available from SGL Carbon Group as C10 M250 UNS, which is a milled carbon fiber having a fiber diameter of about 8 μm, a mean fiber length of about 135 μm, and a resistivity of about 18 μOhm, and a fiber density of about 1.75 g/cc.

In certain embodiments of the present disclosure, where the plurality of conductive particles comprise carbon black as a first species and carbon fiber as a second species, the weight ratio of carbon black to carbon fiber ranges from about 1:1 to 5:1. For example, one preferred ratio is approximately 4:1. In certain embodiments where the first conductive particle species is a large particle size carbon black and the second conductive particle species is a carbon fiber, the sensor film exhibits a base resistance of less than or equal to about 50 mOhms.

In Table 2, experimental data reflects comparison of sensors comprising a plurality of conductive particles, where a large particle diameter low surface area carbon black is a first species and a pelletized carbon fiber is a second species, as compared to Control sensors not having multiple species of conductive particles. The results in Table 2 display various parameters related to sensor operation and sensitivity to exposure to 50% LFL Cyclohexene. All of the controls and examples described herein are prepared with 3-5% vinylmethylsiloxane-35-75% octylmethylsiloxane-20-62% dimethylsiloxane terpolymer (available as VAT 4326 from Gelest) with SIP 6829 (a platinum carbonyl cyclovinylmethylsiloxane catalyst complex). They were each prepared on PV-Probes, similar to those shown in FIG. 1, applied and cured for 8 hours at 130° C. Control 4 contains a carbon black particle used in chemiresistor sensors having an $N_2$ value of about 14 $m^2$/g and a DBP of 85 ml/100 g and is commercially available as 15HS from Asahi Carbon Company.

Example C is a sensor film matrix in accordance with certain embodiments of the present disclosure, comprising 75 phr of Asahi 15HS carbon black (a large particle size carbon black available from Asahi Carbon Company having an $N_2$ value of about 14 $m^2$/g and a DBP of 85 ml/100 g) and 73 phr of milled carbon fiber, specifically with C10 M250 UNS from SGL Carbon, where the mixture of the plurality of conductive particles is provided in the polymer matrix at 148 phr, with the polymer system described in Control 4. Example D is a mixture of carbon black and carbon fibers, where the amount of carbon black to carbon fiber is approximately 139.1:32.1 on a phr basis, or about 80% carbon black and about 20% carbon fiber and the conductive particles are mixed with the polymer at 171 phr. Example E is likewise a mixture of carbon black and carbon fibers also at approximately 148.2:34.2 on a phr basis, where the conductive particles are added to the sensor matrix at 182 phr. Example F is likewise a mixture of carbon black and carbon fibers also at approximately 130:30 on a phr basis, where the conductive particles are added to the sensor matrix at 160 phr. It should be noted that it was attempted to prepare a sample having solely milled carbon fibers, specifically milled C10 M250 UNS fibers, however, the sample was not processable, as it was too dry to form a sensor film on a probe surface.

As shown in Table 2, the blends of large particle size carbon black and carbon fibers of Examples C, D, E and F demonstrate significant reductions in the resistance of the sensor film matrix. As previously described above, maximizing the vapor ratio and minimizing the temperature ratio are desirable for sensor film design. Examples D and E show comparable vapor ratios to the carbon black Control 4. Further, the temperature ratios are slightly lower for Example F, the benefit of a significant reduction in the resistance is gained.

generally described by the structural repeating unit (—O—SiRR'—)$_n$, where R and R' may be the same or different side constituent groups, and n may be any value above 2 designating the repetition of the SRU in the polymer backbone. Thus, such siloxane polymers generally comprise at least one siloxane monomer or SRU. Siloxane polymers are also known in the art as "silicone" polymers. Siloxane polymers may include polyheterosiloxanes, where side groups and/or structural repeating units may be different entities (having different side constituent groups), such as, for example, the siloxane co-polymer described by the nominal SRU formula, (—O—SiRR')$_n$—(—O—Si—R"R'")$_m$, wherein R and R' are

TABLE 2

|  | Control 4 | Example C | Example D | Example E | Example F |
|---|---|---|---|---|---|
| 3-5% vinylmethylsiloxane - 35-75% octylmethylsiloxane - 20-62% dimethylsiloxane terpolymer (phr) | 81.46 | 81.46 | 81.46 | 81.46 | 85.867 |
| 7-13% Hydromethylsiloxane - 87-93% octylmethylsiloxane copolymer (phr) | 18.5 | 18.5 | 18.5 | 18.5 | 14.133 |
| Catalyst SIP 6829 | 0.45 | 0.45 | 0.45 | 0.45 | 0.45 |
| Carbon Black (phr) | 144 | 75 | 139.1 | 148.2 | 130 |
| Carbon Fiber (phr) | — | 73 | 32.1 | 34.2 | 30 |
| Resistance at 0 seconds (kOhm) | 23.2 | 0.43 | 0.36 | 0.37 | 0.107 |
| Resistance at 20 seconds (kOhm) | 636.8 | 2.5 | 7.3 | 9.7 | 0.81 |
| Resistance at 25° C. (kOhm) | 30.4 | 0.42 | 0.36 | 0.37 | 0.308 |
| Resistance at 65° C. (kOhm) | 70.6 | 1.2 | 1.2 | 1.2 | 0.371 |
| Vapor Ratio | 27.4 | 5.9 | 19.9 | 26.0 | 7.6 |
| Temperature Ratio | 2.3 | 2.8 | 3.2 | 3.2 | 1.20 |

As appreciated by those of skill in the art, the plurality of conductive particles may comprise additional species than just the first and second species. Thus, the plurality of conductive particles may contain three or more distinct species of conductive particles, creating various blends of conductive particles. Other exemplary suitable conductive particles 62 that can be used with the present disclosure, as recognized by one of skill in the art, such as, for example, platinum, nickel coated graphite fiber (NCGF), graphite (i.e., hexagonally crystallized carbon), other carbon blacks not described above, conductive metal borides, nitrides or carbides. Further, the total amount of the plurality of conductive particles added is dependent on the individual characteristics of the particle selected, but can range from about 25 to about 75 percent by weight of the total mixture. Distribution of the conductive particles 62 throughout the polymer base 60 can be achieved by mixing the conductive particles 62 into a polymer mixture prior to application on the sensor probe 12 to form a matrix mixture which forms the polymer base 60 of the sensor film 22. Preferably, the conductive particles 62 are homogeneously distributed throughout the polymer matrix base 60 to enhance the uniformity of resistance measurements, as discussed above.

In various embodiments of the present disclosure, the sensor film 22 comprises a polymer resin comprising siloxane. A "siloxane polymer" as used herein, refers to a cross-linked polymer that has a basic backbone of silicon and oxygen with side constituent groups that may be the same or different, distinct side groups from R" and R'". Further R and R' may be different from one another, likewise the same may be true for R" and R'". Such siloxane polymers may terminate in any variety of terminal groups, such as for example, trimethyl silyl ((CH$_3$)$_3$Si) terminated siloxane, or ethyl vinyl terminated siloxane.

In one preferred embodiment of the present disclosure, the polymer of the sensor film is a cross-linked dimethylsiloxane (—O—SiRR')$_n$, where R and R' are both CH$_3$. Such side groups may be referred to as "branched" indicating side groups attached to the siloxane backbone.

In an alternate preferred embodiment of the present disclosure, the sensor film 22 comprises a crosslinked siloxane polymer base, wherein the siloxane polymer backbone has at least one monomer with a large hydrocarbon substituted side group represented by R' in the nominal general formula for the structural repeating unit (—O—SiRR')$_n$. A "hydrocarbon side group", as used herein, includes any hydrocarbon or hydrocarbon derived side group with two carbon atoms or greater. Examples of such hydrocarbon side groups include: alkyl and aryl groups greater than an ethyl group, branched alkyl groups, aromatics, modified hydrocarbon compounds comprising a polar groups, or mixtures thereof. Polar group modified hydrocarbons incorporate a polar molecule or molecular group into the hydrocarbon side group structure, with the effect of imparting polarity on the entire side group. Such polar atoms or groups may include, for example, oxygen, nitrogen, or ammonia, cyano or hydroxyl groups.

Examples of preferred hydrocarbon side groups include without limitation: ethyl, propyl, butyl, pentyl, hexyl, heptyl, octyl, nonyl, decyl, phenyl, alkylphenyl, cyclopentyl, and phenylpropyl. Particularly preferred hydrocarbon side groups are alkyl groups with eight or more carbon atoms (octyl groups or higher). Other preferred hydrocarbon side groups comprising a polar group include, for example, butylated aryloxypropyl, N-pyrrolidonepropyl, cyanopropyl, benzyltrimethyl ammonium chloride and hydroxyalkyl.

One example of such a siloxane having a large hydrocarbon side group includes an octyl hydrocarbon side group that forms an octylmethylsiloxane monomer. It is preferable that the siloxane polymer according to the present embodiment is crosslinked, and thus also contains a functional group capable of crosslinking during any subsequent curing or crosslinking processes. Preferred crosslinked siloxane polymers include those polymers (including homopolymers and copolymers) having at least one large hydrocarbon side substituent group. As used herein, the term "polymer" encompasses homopolymers and copolymers. The term "copolymer" generically refers to a polymeric structure that has two or more monomers polymerized with one another, and includes polymers such as terpolymers with three combined monomers. A "homopolymer" refers to a polymer comprised of a single monomer. One example of a preferred crosslinked siloxane having a copolymer (e.g., terpolymer) structure is poly(vinylmethylsiloxane-octylmethylsiloxane-dimethylsiloxane). Thus, the terpolymer structure has vinyl functional groups that are capable of crosslinking when exposed to crosslinking or curing agents. Ranges of the quantity of monomers in the terpolymer include (3-5% vinylmethylsiloxane)-(35-75% octylmethysiloxane)-(20%-62% dimethylsiloxane), wherein the octyl is the hydrocarbon side group, R', incorporated into the siloxane monomer, and R is a methyl side group. Another example of a preferred crosslinked siloxane having a large hydrocarbon side group according to the present disclosure is a polyphenylmethylsiloxane, where the phenyl is the large hydrocarbon side group and the polymer has vinyl terminal groups for subsequent crosslinking.

In certain embodiments, the terpolymer having a large hydrocarbon side group is further reacted with another polymer. Preferably, this additional polymer likewise comprises siloxane, and may be a homopolymer or copolymer, as described above, with functional groups capable of crosslinking. Thus, in a certain embodiment of the present disclosure, the additional copolymer comprises a polydimethyl siloxane. In another embodiment, the additional copolymer comprises a siloxane copolymer further comprising an additional large hydrocarbon side group. For example, one suitable polymer comprises (7-13% hydromethylsiloxane)-(87-93% octylmethylsiloxane) and has an average molecular weight of about 6000, and is capable of cross-linking with the first terpolymer described above.

Incorporation of large hydrocarbon side groups into monomers (which are further incorporated into polymers according to the present disclosure) is achieved by polymerization performed in a conventional manner. Such a monomer, having a side group, is preferably functionalized by incorporating a reactive functional group (e.g., epoxy, amine, mercapto, methacrylate/acrylate, acetoxy, chlorine; hydride or vinyl; or hydroxyl groups) to facilitate incorporation into the siloxane backbone by polymerization, such as by conventional methods known in the art. In the case of poly(vinylmethylsiloxane-octylmethylsiloxane-dimethylsiloxane), discussed above, the octylmethylsiloxane monomer is incorporated into a copolymer with other monomers of dimethylsiloxane and vinylmethyl siloxane, where the octylmethylsiloxane monomer is preferably present in the range of from about 35% to about 75%. The octylmethylsiloxane monomer displaces the dimethylsiloxane monomer. In the case of polyphenylmethylsiloxane, substantially all of the polymer chain comprises the phenylmethylsiloxane monomer, except for the terminal ends of the siloxane polymer which are vinyl terminated (e.g., dimethylvinyl terminated siloxane). Such monomer ranges are exemplary and non-limiting and are dependent upon specific characteristics of the individual monomers employed. It is preferable to maximize the quantity of large hydrocarbon side group substituted monomers in the siloxane polymer, because maximizing the amount of large hydrocarbon side groups in a siloxane based polymer sensor film has been shown to increase the overall temperature stability and analyte sensitivity.

After the large hydrocarbon side group siloxane base copolymer (or plurality of distinct copolymers) is formed (by a conventional polymerization reaction), the polymer(s) further undergo cross-linking after incorporation into the sensor film. Such crosslinking may be carried out by conventional means, such as by exposure to irradiation or peroxide, moisture cure by a condensation reaction, or a hydrosilylation reaction in the presence of a catalyst. Any method of crosslinking siloxane polymers may be used with the present disclosure, as recognized by one of skill in the art. A preferred method of crosslinking is the hydrosilylation reaction in the presence of a catalyst, which can generally be conducted at lower temperatures and where the control over the degree of crosslinking is greater.

Crosslinking by hydrosilylation generally requires a catalyst and a crosslinking (curing) reagent which reacts with accessible functional groups on at least some of the side groups within the siloxane polymer. One example of a hydrosilylation crosslinking reaction includes, for example, polyethylhydrosiloxane and hydromethylsiloxane octylmethylsiloxane copolymer as a crosslinking reagent in the presence of a platinum catalyst to result in a crosslinked siloxane polymer. Polyethylhydrosiloxane is commercially available as the product HES-992, from Gelest, Inc. of Tullytown, Pa. The hydrosilylation reaction facilitates crosslinking between neighboring siloxane chains at the functional group sites. Other feasible catalyst systems that may be used for hydrosilylation (in addition to platinum) in the present disclosure include, for example: platinum carbonyl cyclovinylmethyliloxane complex used for elevated cures, such as SIP 6829 which is also commercially available from Gelest, Inc.; Rh(l) catalysts such as $(PPh_3)_3RhCl$ or $[(C_2H_4)_2RhCl]_2$, Ni catalysts, $(PPh_3)PdCl_2$, $Rh_2(OAc)_4$, $Ru_3(CO)_{12}$, and $Co_2(CO)_8$ and equivalents thereof. Functional groups must be present along the siloxane backbone or at the chain ends to allow for subsequent crosslinking after polymerization. The distinct monomers within any of the copolymers may be distributed randomly or may be regularly ordered.

Testing of such sensor films 22 according to the various embodiments of the present disclosure have demonstrated both increased temperature stability and analyte sensitivity, as well as reduced resistance when compared with known chemiresistor sensor films.

A preferred method of making the present disclosure includes forming the large hydrocarbon side group siloxane polymer by reacting a siloxane monomer having a functionalized hydrocarbon group with other siloxane monomers to polymerize the monomers together to form a copolymer. As previously discussed, preferably the resulting polymer structure is designed to have additional functional groups that facilitate subsequent crosslinking by a conventional hydrosilyation reaction, as recognized by one of skill in the art. In certain embodiments, the copolymer forms a first part of the polymer system and a second part comprises a second copolymer or homopolymer comprising siloxane. The polymer of the second part can also comprise a large hydrocarbon side group, and during the crosslinking reaction, the first part polymer is cross-linked with the second part polymer.

As previously discussed, the crosslinking reaction is preferably achieved through a hydrosilyation reaction by adding an appropriate curing reagent and a catalyst. The rate of reaction for crosslinking is dependent on temperature and is accelerated when temperature is raised; a catalyst is added; or both. Temperature may be used to control the rate of reaction to coincide with processing needs. Further, the addition of the catalyst may be prolonged until the mixture is ready to be processed for application onto the sensor. Preferably, the curing reagent is added in the range of about 1 to about 5 weight % of the total polymer and curing reagent to form a polymer mixture. Preferably, catalyst is charged to the polymer mixture from about 0.05 to 1 weight percent of the total polymer mixture (excluding conductive particles).

A matrix mixture may be formed by admixing the plurality of conductive particles pre-mixed with the first and second species to the polymer mixture prior to charging with the catalyst. The plurality of conductive particles are added in a range of from about 25 to about 75% of the total mixture depending on particle characteristics, including tendency to disperse in the matrix. It is preferred that the plurality of conductive particles is well mixed into the polymer mixture for even distribution. The polymer or matrix mixture can be blended or mixed by equipment known in the art, such as and not limited to for example, a mixer (e.g., a Banbury® or Brabender® mixer), a kneader, a monoaxial or biaxial extruder (e.g., single-screw or twin-screw extruders).

The handling and flowability of a matrix mixture is dependent on the rate of crosslinking once the catalyst is added, which affects the viscosity of the mixture. The amount of time that remains for handling is generally known as the "pot life", and may range from many hours at room temperature to less than an hour if temperatures are raised to above room temperature. The crosslinking or curing reaction may be prolonged by addition of inhibitors, which are well known in the art, as a means for retarding the reaction. The crosslinking or curing reaction can be performed entirely at room temperature, or may be accelerated by heating the mixture, depending on the processing needs. Such curing temperatures range from about 30° C. to about 250° C. The mixture is then applied to the sensor surface by conventional application means (e.g., doctor blade, casting, lamination, extrusion, pad printing, spraying or silk screening). After application, further sensor components and processing may be completed, such as applying a protective cap. Curing occurs by any conventional methods known in the art, for example, by placing the sensor having an applied matrix mixture applied into an oven at elevated temperature, for example, for 3 to 8 hours at 120° C. to 130° C. However, many variations of curing the siloxane polymer in the matrix mixture are feasible with the present disclosure.

EXAMPLE 1

A sensor film having a cross-linked large hydrocarbon side group substituted siloxane polymer matrix with a first species of conductive particle as a large particle size conductive carbon black and a second species of carbon fibers is prepared by adding the following materials into a mixer: 4.45 grams of VAT-4326 a (3-5% vinylmethylsiloxane)-(45-52% octylmethylsiloxane)-(dimethylsiloxane) terpolymer available from Gelest, 3.23 grams (7-13% hydromethylsiloxane)-(87-93% octylmethylsiloxane) copolymer; 19.31 grams of Asahi 15HS (a large particle size carbon black available from Asahi Carbon Company having an $N_2$ value of 14 $m^2$/g and a DBP of 85 ml/100 g), 4.46 grams of C10 M250 UNS (a milled carbon fiber available from SGL Carbon Group), 0.08 grams of SIP 6829 (a platinum carbonyl cyclovinylmethylsiloxane catalyst complex). The materials are mixed in a Brabender® mixer for 15 minutes at 30° C. and 80 rpm to form a matrix mixture. The mixture is then applied in a groove over electrodes in a sensor structure. The sensor structure having the matrix mixture applied is then cured for 8 hours at 130° C.

EXAMPLE 2

A sensor film having a cross-linked large hydrocarbon side group substituted siloxane polymer matrix with a first species of conductive particle as a large particle size conductive carbon black and a second species comprising nickel is prepared by adding the following materials into a mixer: 0.11 grams of VAT-4326 a (3-5% vinylmethylsiloxane)-(45-52% octylmethylsiloxane)-(dimethylsiloxane) terpolymer available from Gelest, 10.3 grams (7-13% hydromethylsiloxane)-(87-93% octylmethylsiloxane) copolymer; 18.5 grams of Asahi 15HS (a large particle size carbon black available from Asahi Carbon Company having an $N_2$ value of 14 $m^2$/g and a DBP of 85 ml/100 g), 4.0 grams of Type 210 nickel (fine nickel powder Type 210 from Inco Ltd. a subsidiary of Novamet); 0.086 grams of SIP 6829 (a platinum carbonyl cyclovinylmethylsiloxane catalyst complex). The materials are mixed in a Brabender® mixer for 15 minutes at 30° C. and 80 rpm to form a matrix mixture. The mixture is then applied in a groove over electrodes in a sensor structure. The sensor structure having the matrix mixture applied is then cured for 8 hours at 130° C.

EXAMPLE 3

A sensor film having a cross-linked large hydrocarbon side group substituted siloxane polymer matrix with a first species of conductive particle as a large particle size conductive carbon black and a second species comprising nickel is prepared by adding the following materials into a mixer: 0.11 grams of VAT-4326 a (3-5% vinylmethylsiloxane)-(45-52% octylmethylsiloxane)-(dimethylsiloxane) terpolymer available from Gelest, 10.2 grams (7-13% hydromethylsiloxane)-(87-93% octylmethylsiloxane) copolymer; 18.4 grams of Asahi 15HS (a large particle size carbon black available from Asahi Carbon Company having an $N_2$ value of 14 $m^2$/g and a DBP of 85 ml/100 g), 4.6 grams of Type 210 nickel (fine nickel powder Type 210 from Inco Ltd. a subsidiary of Novamet); 0.085 grams of SIP 6829 (a platinum carbonyl cyclovinylmethylsiloxane catalyst complex). The materials are mixed in a Brabender® mixer for 15 minutes at 30° C. and 80 rpm to form a matrix mixture. The mixture is then applied in a groove over electrodes in a sensor structure. The sensor structure having the matrix mixture applied is then cured for 8 hours at 130° C.

EXAMPLE 4

A sensor film having a cross-linked large hydrocarbon side group substituted siloxane polymer matrix with a first species of conductive particle as a large particle size conductive carbon black and a second species comprising nickel is prepared by adding the following materials into a mixer: 3.7 grams of VAT-4326 a (3-5% vinylmethylsiloxane)-(45-52% octylmethylsiloxane)-(dimethylsiloxane) terpolymer available from Gelest, 6.7 grams (7-13% hydromethylsiloxane)-(87-93% octylmethylsiloxane) copolymer; 18.5 grams of Asahi 15HS (a large particle size carbon black available from Asahi Carbon Company having an $N_2$ value of 14 $m^2$/g and a DBP of 85 ml/100 g), 4.0 grams of Type 210 nickel (fine nickel powder Type 210 from Inco Ltd. a subsidiary of Novamet); 0.086 grams of SIP 6829 (a platinum carbonyl cyclovinylmethylsiloxane catalyst complex). The materials are mixed in a Brabender® mixer for 15 minutes at 30° C. and 80 rpm to form a matrix mixture. The mixture is then applied in a groove over electrodes in a sensor structure. The sensor structure having the matrix mixture applied is then cured for 8 hours at 130° C.

EXAMPLE 5

A sensor film having a cross-linked large hydrocarbon side group substituted siloxane polymer matrix with a first species of conductive particle as a large particle size conductive carbon black and a second species comprising nickel is prepared by adding the following materials into a mixer: 3.7 grams of VAT-4326 a (3-5% vinylmethylsiloxane)-(45-52% octylmethylsiloxane)-(dimethylsiloxane) terpolymer available from Gelest, 6.6 grams (7-13% hydromethylsiloxane)-(87-93% octylmethylsiloxane) copolymer; 18.4 grams of Asahi 15HS (a large particle size carbon black available from Asahi Carbon Company having an $N_2$ value of 14 $m^2$/g and a DBP of 85 ml/100 g), 4.6 grams of Type 210 nickel (fine nickel powder Type 210 from Inco Ltd. a subsidiary of Novamet); 0.086 grams of SIP 6829 (a platinum carbonyl cyclovinylmethylsiloxane catalyst complex). The materials are mixed in a Brabender® mixer for 15 minutes at 30° C. and 80 rpm to form a matrix mixture. The mixture is then applied in a groove over electrodes in a sensor structure. The sensor structure having the matrix mixture applied is then cured for 8 hours at 130° C.

Figure 7:
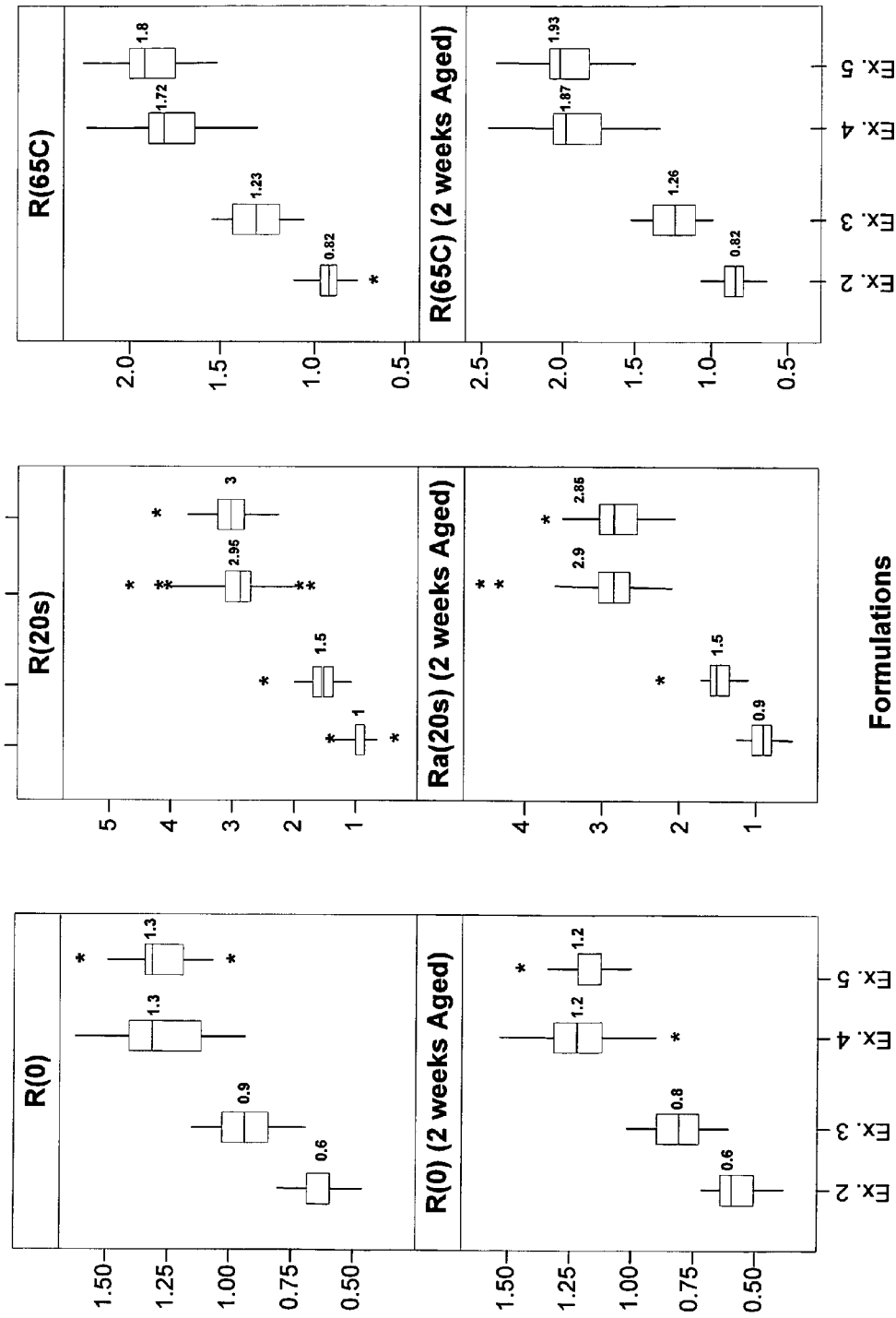
FIG. 7 is a chart showing temperature and vapor ratios of various embodiments of the present disclosure comprising both carbon black and nickel conductive particles.
Figure 8:
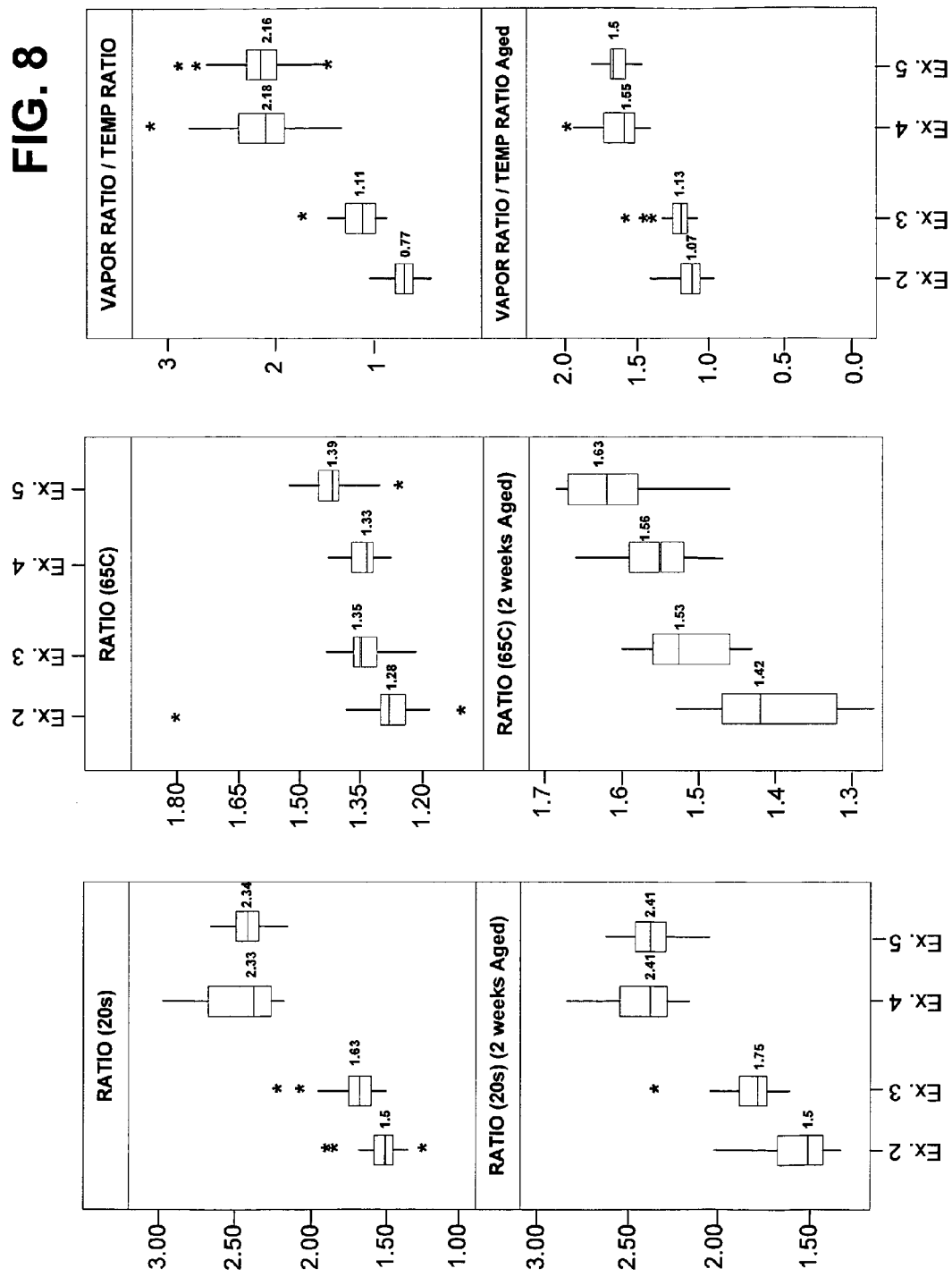
FIG. 8 is a chart showing temperature and vapor ratios of various embodiments of the present disclosure comprising both carbon black and nickel conductive particles.

The use of nickel particles as one of the species of conductive particles has enabled a low resistance sensor film, as is demonstrated in FIGS. 7 and 8, showing testing with Examples 2-5 (the data in FIGS. 7 and 8 was generated by testing 30 devices respectively prepared in accordance with Examples 2-4). Further, the data shown in FIGS. 7 and 8 includes testing done shortly after curing the sensor films on the probes and testing after 2 weeks of aging.

FIGS. 7 and 8 show sensor films of Examples 2, 3, 4 and 5, prepared in accordance with the present disclosure, each having a blend of carbon black and nickel particles. FIG. 7 shows the resistance of respective sensor films, tested similarly to that described above in the context of Table 2. FIG. 8 show the ratio of resistance at 20 seconds, at 65° C. and also vapor temperature ratio. As described above, the Vapor Ratio is calculated by taking the measurement of the resistance of the sensor film upon exposure to a target analyte at 0 seconds and 20 seconds, and dividing the 20 second resistance value by the 0 second value. Preferably, the vapor ratio is maximized as much as possible. For establishing the temperature ratio, the resistance is measured at a first temperature of 25° C. and a second temperature of 65° C., where the temperature ratio is the resistance value at 65° C. divided by the resistance value at 25° C. Ideally, the temperature ratio approaches zero to reflect no variations in resistance which are attributed to changes in temperature.

EXAMPLE 6

A sensor film having a cross-linked large hydrocarbon side group substituted siloxane polymer matrix with a first species of conductive particle as a large particle size conductive carbon black and a second species of high conductivity carbon black is prepared by adding the following materials into a mixer: 18.31 grams of VAT 4326 a (3-5% vinylmethylsiloxane)-(45-52% octylmethylsiloxane)-(dimethylsiloxane) terpolymer available from Gelest, 7.79 grams (7-13% hydromethylsiloxane)-(87-93% octylmethylsiloxane) copolymer; 12.71 grams of Asahi 15HS (a large particle size carbon black available from Asahi Carbon Company having an $N_2$ value of 14 $m^2$/g and a DBP of 85 ml/100 g), 1.36 grams of KETJEN® EC 300 J (a high conductivity carbon black available from Azko Nobel having a DBP of 365 ml/100 g ), and 0.12 grams of SIP 6829. The materials are mixed in a Brabender® mixer for 15 minutes at 30° C. and 80 rpm to form a matrix mixture. The mixture is then applied in a groove over electrodes in a sensor structure. The sensor structure having the matrix mixture applied is then cured for 8 hours at 130° C.

EXAMPLE 7

A sensor film having a cross-linked large hydrocarbon side group substituted siloxane polymer matrix with a first species of conductive particle as a large particle size conductive carbon black and a second species of high conductivity carbon black is prepared by adding the following materials into a mixer: 18.31 grams of VAT 4326 a (3-5% vinylmethylsiloxane)-(45-52% octylmethylsiloxane)-(dimethylsiloxane) terpolymer available from Gelest, 7.79 grams (7-13% hydromethylsiloxane)-(87-93% octylmethylsiloxane) copolymer; 14.25 grams of Asahi 15HS (a large particle size carbon black available from Asahi Carbon Company having an $N_2$ value of 14 $m^2$/g and a DBP of 85 ml/100 g), 1.0 grams of KETJEN® EC 600 JD (a high conductivity carbon black available from Azko Nobel having a DBP of 495 ml/100 g), and 0.11 grams of SIP 6829. The materials are mixed in a Brabender® mixer for 15 minutes at 30° C. and 80 rpm to form a matrix mixture. The mixture is then applied in a groove over electrodes in a sensor structure. The sensor structure having the matrix mixture applied is then cured for 8 hours at 130° C.

Figure 9:
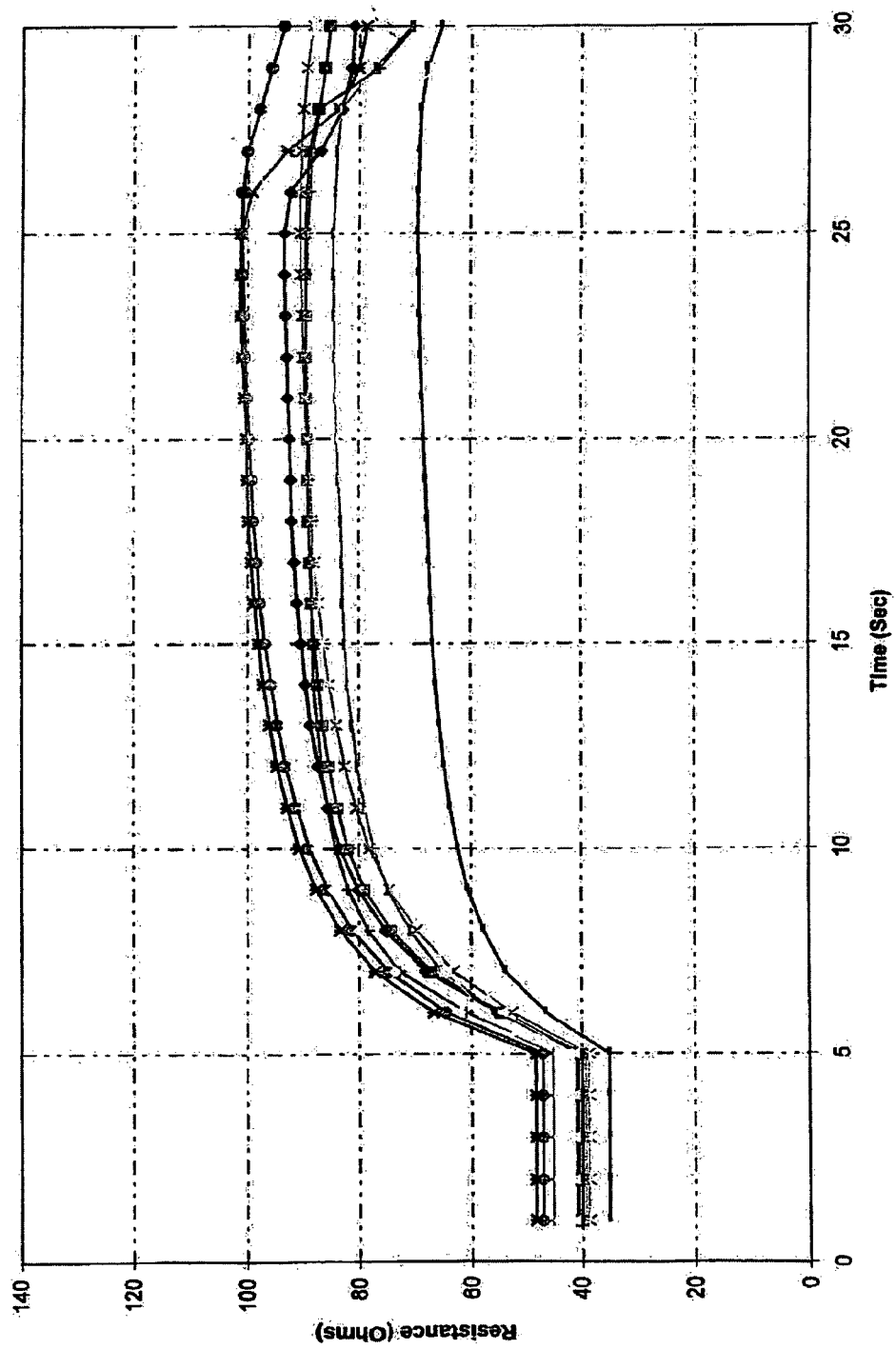
FIG. 9 is a chart showing resistance over time for a sensor film composition in the presence of target analytes for one embodiment of the present disclosure having both low conductivity and high conductivity carbon black particles.
Figure 10:
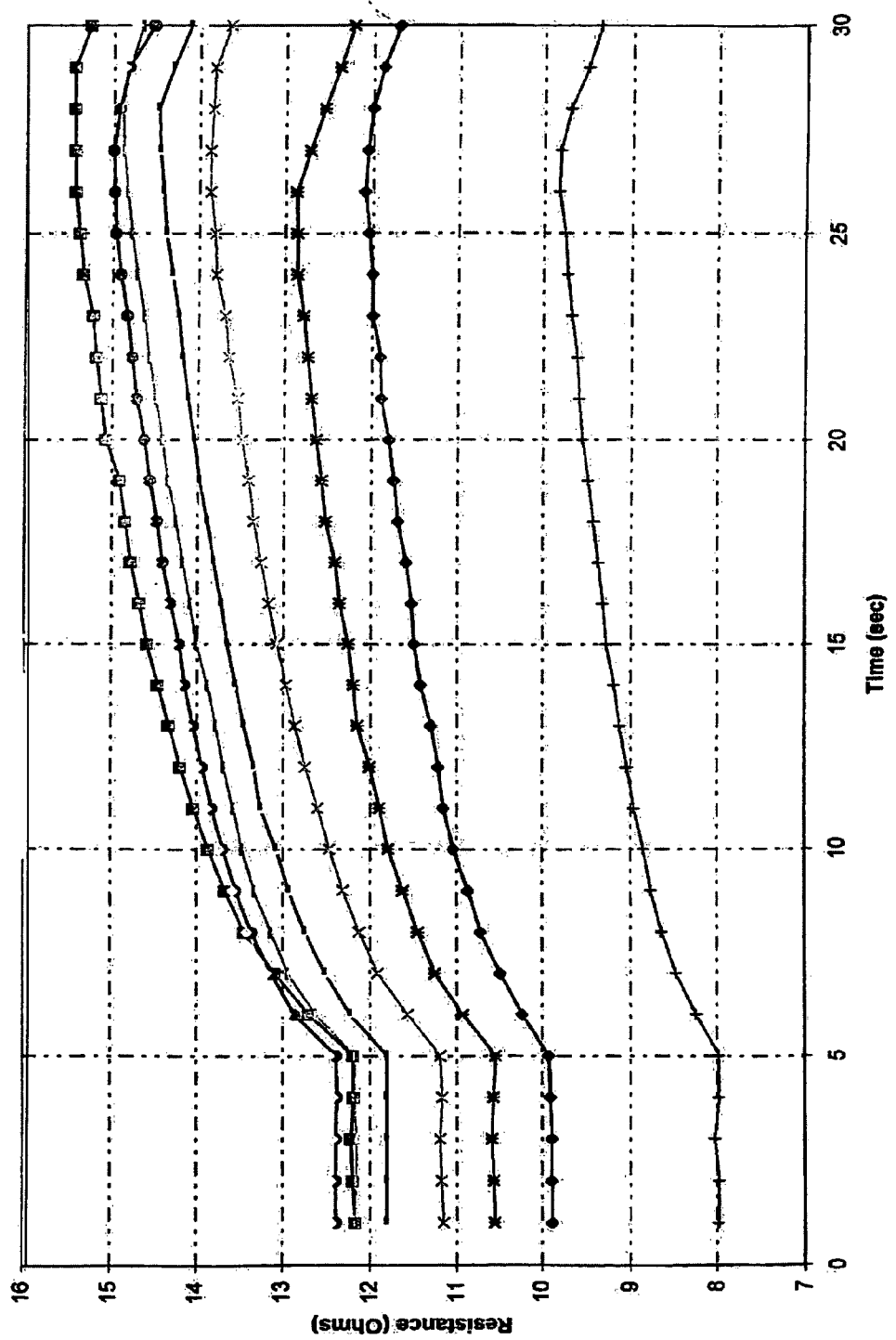
FIG. 10 is a chart showing resistance over time for a sensor film composition in the presence of target analytes for another embodiment of the present disclosure having both low conductivity and high conductivity carbon black particles.

FIGS. 9 and 10 show Examples 6 and 7, sensor films prepared in accordance with the present disclosure, each having a combination of low conductivity and high conductivity carbon black particles. FIGS. 9 and 10 show the resistance of respective sensor films, tested similarly to that described above in the context of FIG. 6. The high conductivity carbon black is KETJEN® Black EC 300J and shows a maximum resistance of just over 100 Ohm in FIG. 9.

FIG. 10 shows the resistance of a sensor matrix film comprising a high conductivity carbon black particle, KETJEN® Black EC 600 JD. As can be observed, the maximum resistance of the sensor film is less than about 16 Ohm. Both of the sensors in FIGS. 9 and 10 exhibit a change in resistance when exposed to target analytes, where the change in resistance is significantly less than 1 kOhm. Sensor films prepared in accordance with Example 6 have resistance of less than about 125 Ohm, and sensor films prepared in accordance with Example 7 have sensor films with a resistance of less than 16 Ohm.

The sensor films according to the present disclosure provide a robust low resistance sensor having good stability during temperature fluctuations, thus ensuring the accuracy of the sensor readings of analyte concentration by making it less dependent on variations in temperature. Thus, the fundamental trade-off between temperature sensitivity and sensitivity to analytes has been improved. The present disclosure provides increased sensitivity to target analytes over the prior art sensor films, improving the sensor film operation. Further, the sensors have increased energy efficiency and robustness, and can be used in low current/resistance applications. The description of the disclosure and examples provided herein is merely exemplary in nature and, thus, variations that do not depart from the gist of the disclosure are intended to be within the scope of the disclosure. Such variations are not to be regarded as a departure from the spirit and scope of the disclosure.

What is claimed is:

1. A conductometric sensor film for detecting one or more chemical analytes comprising:
a polymer matrix comprising a crosslinked polymer and a plurality of conductive particles homogeneously distributed within said matrix; wherein said crosslinked polymer comprises a siloxane monomer; wherein said plurality comprises at least two distinct species of conductive particles, where a first species of said conductive particles comprises carbon black having an $N_2$ adsorption of between about 8 to about 25 $m^2/g$ and a DBP of about 1 to about 180 ml/100 g, wherein the sensor film exhibits a change in resistance in the presence of the one or more chemical analytes.

2. The conductometric sensor film according to claim 1, wherein a second species of said plurality of conductive particles is selected from the group consisting of nickel, gold, silver, manganese, copper, iron, cobalt, magnesium, aluminum, and mixtures and alloys thereof.

3. The conductometric sensor film according to claim 1, wherein said second species of said conductive particles comprises nickel.

4. The conductometric sensor film according to claim 3, wherein the sensor film has a base resistance of less than or equal to about 700 Ohms.

5. The conductometric sensor film according to claim 3, wherein said conductive particles comprising nickel have an average particle size of less than about 500 nm.

6. The conductometric sensor film according to claim 3, wherein a ratio of said first species to said second species of conductive particles comprising nickel is from about 3:1 to about 10:1 on a weight basis.

7. The conductometric sensor film according to claim 1, wherein a second species of said plurality of conductive particles comprises a particle having an axial geometry.

8. The conductometric sensor film according to claim 7, wherein said axial geometry particle comprises a carbon fiber.

9. The conductometric sensor film according to claim 8, wherein the sensor has a base resistance of less than or equal to about 50 mOhms.

10. The conductometric sensor film according to claim 1, wherein said first species of said plurality of conductive particles has a first resistance that is greater than a second resistance of said second species of said plurality of conductive particles.

11. The conductometric sensor film according to claim 10, wherein a ratio of said low conductivity first species to said high conductivity second species is from about 8:1 to about 15:1 on a weight basis.

12. The conductometric sensor film according to claim 1, wherein said second species comprises a high conductivity carbon black.

13. The conductometric sensor film according to claim 12, wherein the sensor film has a base resistance of less than or equal to about 50 Ohms.

14. The conductometric sensor film according to claim 1, wherein said plurality of conductive particles comprises at least one conductive particle selected from the group consisting of: nickel, gold, platinum, silver, manganese, copper, iron, cobalt, magnesium, aluminum, and alloys thereof, conductive metal borides, nitrides and carbides, conductive whiskers, wires, fibers, and filaments, carbon black, graphite, and mixtures thereof.

15. The conductometric sensor film according to claim 1, wherein said siloxane monomer has at least one hydrocarbon side group with greater than or equal to two carbon atoms.

16. The conductometric sensor film according to claim 1, wherein said crosslinked polymer comprises an octylmethylsiloxane monomer.

17. A low resistance conductometric sensor film for detecting one or more chemical analytes comprising:
a polymer matrix comprising a polymer and a plurality of conductive particles homogeneously distributed within said polymer; wherein said polymer comprises a siloxane monomer having at least one hydrocarbon side group with greater than or equal to two carbon atoms; and said plurality comprises at least two distinct species of conductive particles, wherein a first species of said conductive particles comprises carbon black, and wherein the sensor film exhibits a base resistance that is less than or equal to about 700 Ohms.

18. The low resistance conductometric sensor film according to claim 17, wherein said carbon black has an $N_2$ adsorption of between about 8 to about 25 $m^2/g$, a DBP of about 1 to about 180 ml/100 g.

19. The low resistance conductometric sensor film according to claim 17, wherein said second species comprises an axial geometry particle comprising carbon.

20. The low resistance conductometric sensor film according to claim 17, wherein said second species comprises a conductive particle selected from the group consisting of nickel, gold, silver, manganese, copper, iron, cobalt, magnesium, aluminum, and mixtures and alloys thereof.

21. The low resistance conductometric sensor film according to claim 17, wherein said first species of said plurality of conductive particles has a first resistance that is greater than a second resistance of said second species of said plurality of conductive particles.

22. A low resistance conductometric sensor film for detecting one or more chemical analytes comprising:
a polymer matrix comprising a polymer and a plurality of conductive particles homogeneously distributed within said polymer; wherein said polymer comprises a siloxane monomer having at least one hydrocarbon side group with greater than or equal to two carbon atoms; and said plurality comprises at least two distinct species of conductive particles, wherein a first species of said conductive particles comprises carbon black having an $N_2$ adsorption of between about 8 to about 25 $m^2/g$ and a DBP of about 1 to about 180 ml/100 g, and a second species is selected from the group consisting of: high conductivity carbon black, a conductive axial geometry particle comprising carbon, and particles comprising nickel, wherein the sensor film has a base resistance of less than or equal to about 700 Ohms and the sensor film exhibits a change in resistance in the presence of one or more chemical analytes.

* * * * *

UNITED STATES PATENT AND TRADEMARK OFFICE
CERTIFICATE OF CORRECTION

PATENT NO. : 7,645,422 B2
APPLICATION NO. : 11/510942
DATED : January 12, 2010
INVENTOR(S) : Blok et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 656 days.

Signed and Sealed this

Sixteenth Day of November, 2010

David J. Kappos
*Director of the United States Patent and Trademark Office*